Figure 1:
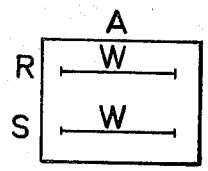
Figure 1:
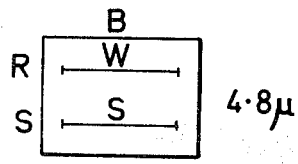
Figure 1:
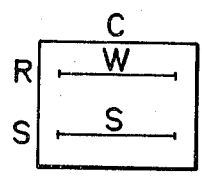
Figure 1:
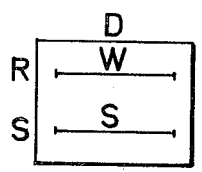
Figure 1:
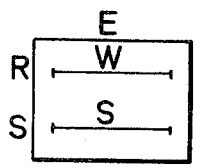
Figure 1:
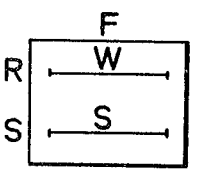

United States Patent [19]

Hopkins et al.

[11] 4,207,469

[45] Jun. 10, 1980

[54] ANALYSIS OF EMULSIONS AND SUSPENSIONS

[75] Inventors: Joseph Hopkins, Cramlington; David McKenna, Tyne and Wear, both of England

[73] Assignee: Sir Howard Grubb Parsons and Company Ltd., Newcastle upon Tyne, England

[21] Appl. No.: 863,429

[22] Filed: Dec. 22, 1977

Related U.S. Application Data

[63] Continuation of Ser. No. 710,704, Aug. 2, 1975, Pat. No. 4,076,983.

[30] Foreign Application Priority Data

Aug. 4, 1975 [GB] United Kingdom ............... 32510/75

[51] Int. Cl.$^2$ .............................................. G01J 1/00
[52] U.S. Cl. .................................. 250/343; 250/339; 250/345
[58] Field of Search ............... 250/343, 565, 341, 339, 250/344, 345; 356/434

[56] References Cited

U.S. PATENT DOCUMENTS

| | | | |
|---|---|---|---|
| 3,730,627 | 5/1973 | Kent | 356/434 |
| 3,839,633 | 10/1974 | McKenna et al. | 250/343 |
| 3,955,096 | 5/1976 | Faulhaber | 250/565 |
| 3,968,367 | 7/1976 | Berg | 250/343 |

Primary Examiner—Alfred E. Smith
Assistant Examiner—Carolyn E. Fields
Attorney, Agent, or Firm—Holman & Stern

[57] ABSTRACT

An apparatus for the quantitative estimation of the dispersion medium and one or more components forming the disperse phase of an emulsion or suspension or mixture thereof, wherein the mean particle size of the disperse phase is less than a selected absorption wavelength of the dispersion medium and also less than a selected absorption wavelength for each of one or more components of the disperse phase, and the said selected absorption wavelength of the dispersion medium is at a wavelength differing substantially from the or each selected absorption wavelength for the disperse phase component or components and the absorption by the or each disperse phase component is stronger than the absorption by the dispersion medium at the selected absorption wavelength for the or each disperse phase component.

The apparatus uses a double beam infrared absorption spectrometer, data storage means, and logic circuitry for providing electronic data equivalents to the natural logarithm of the ratio of the beam energies subsequent to passage through the two test cells.

2 Claims, 2 Drawing Figures

Symbols: R—Reference
W—Water
S—Sample

Optical balance

4·8μ   Water wavelength absorbance stored.

5·7μ   Fat absorbance

6·4μ   Protein absorbance

9·6μ   Lactose absorbance

4·8μ   Total solids content

ANALYSIS OF EMULSIONS AND SUSPENSIONS

This is a continuation of application Ser. No. 710,704, filed Aug. 2, 1975, now U.S. Pat. No. 4,076,983.

This invention relates to the analysis of emulsions and suspensions by means of infra-red absorption methods.

In British Patent specification No. 989,617, a method of analysing emulsions and suspensions is described which is concerned with infra-red absorption techniques for estimation of the disperse phase is emulsions or suspensions or mixtures thereof, together with apparatus for carrying out the method. The method described is particularly suitable for analysis of a plurality of samples of a fluid having the same disperse phase components in differing amounts but in which each sample contains substantially the same proportion of dispersion medium.

In our co-pending British Patent Application No. 36547/72 we describe a similar method of analysis to that of the aforementioned British Patent capable of broader application to samples having substantially differing disperse phase content.

The object of the present invention is to provide an alternative method of analysis to that of the aforesaid co-pending Application capable of similar application whilst allowing simplified apparatus to be employed for carrying the method into effect.

The present invention consists in a method for the quantitative estimation of the dispersion medium and one or more components forming the disperse phase of an emulsion or suspension or mixture thereof, wherein the mean particle size of the disperse phase is less than a selected absorption wavelength of the dispersion medium and also less than a selected absorption wavelength for each of one or more components of the disperse phase, and the said selected absorption wavelength of the dispersion medium is at a wavelength differing substantially from the or each selected absorption wavelength of the disperse phase component or components and the absorption by the or each disperse phase component is stronger than the absorption by the dispersion medium at the selected absorption wavelength for the or each disperse phase component, said method comprising the steps of:

(a) passing a first beam of radiation from a source of infra-red radiation through a sample of fixed path length of the dispersion medium only of an emulsion or suspension to be analysed, and a second beam of the radiation through a second reference sample of fixed path length of the dispersion medium only;

(b) selecting a narrow range of wavelength of radiation from the two beams containing the selected absorption wavelength of the dispersion medium and effecting a balance in the resultant measured energy of the beams subsequent to their passage through the dispersion medium samples for this range of wavelength by way of backing-off means in one channel of multi-channel measuring circuitry reading this range of wavelength only;

(c) successively repeating step (b) for different narrow ranges of wavelength of radiation for each selected absorption wavelength of the remaining components of the disperse phase using in each repetition a separate channel of the multi-channel measuring circuitry associated with the respective narrow range of wavelength chosen;

(d) replacing the sample of dispersion medium in the first beam of radiation by a sample of the emulsion or suspension or mixture thereof to be analysed having the same fixed path length, selecting the same narrow range of wavelength of radiation from the two beams as in step (b) and measuring and storing the absorbance due to the disperse phase of the sample being analysed in terms of the imbalance in the resultant measured energy of the beams subsequent to their passage through the dispersion medium reference sample and the sample being analysed for this range of wavelength;

(e) selecting a narrow range of wavelength of radiation from the two beams containing the selected absorption wavelength of a component of the disperse phase whilst maintaining the sample being analysed in the first beam of radiation and the reference sample of dispersion medium in the second beam of radiation and determining the absorbance due to this component in terms of the resultant absorbance indicated by the measured imbalance of energy in the two beams summated with the product of the stored value from step (d) and the ratio of the absorption coefficient of the dispersion medium at this selected narrow range of wavelength to the absorption coefficient of the dispersion medium at the narrow range of wavelength selected in step (b); and (f) successively repeating step (e) using a different narrow range of wavelength of radiation for each selected absorption wavelength of the remaining components of the disperse phase whilst in each case using the product of the stored value from step (d) with the ratio of the absorption coefficient of the dispersion medium at the narrow range of wavelength selected for the particular disperse phase component determination to the absorption coefficient of the dispersion medium at the narrow range of wavelength selected in step (b).

The invention also consists in a method in accordance with the preceding paragraph in which subsequent to step (f), whilst maintaining the sample being analysed in the first beam of radiation and the reference sample of dispersion medium in the second beam of radiation, the narrow range of wavelength of radiation selected in step (b) is again selected and the total solids content of the disperse phase of the sample being analysed is determined by the measurement as performed in step (d).

The invention also consists in a method in accordance with the first of the preceding two paragraphs in which the total solids content of the disperse phase of the sample being analysed is estimated by summation of the measurements for the individual disperse phase components obtained in steps (e) and (f).

The invention also consists in apparatus for performing the method according to any one of the preceding three paragraphs.

The invention also consists in apparatus according to the preceding paragraph comprising a double beam optical analysis arrangement in combination with measuring and calculating equipment capable of storing data obtained from the optical analysis arrangement and performing mathematical operations utilising the stored data.

The invention also consists in apparatus for the quantitative estimation of the dispersion medium and one or more components forming the disperse phase of an emulsion or suspension or mixture thereof comprising a double beam, infra-red absorption spectrometer instrument having an infra-red source, beam splitting means providing two beam paths of infra-red radiation from the source, a first sample cell disposed in a first of the beam paths and a second sample cell disposed in the second of the beam paths, re-combination means for the beams subsequent to their passage through the cells to provide a single re-combined beam path, a beam chopping device interacting with the two beam paths prior to recombination, narrow range wavelength selection means positioned to limit the wavelength range of radiation in the re-combined beam path, a detector for converting the optical data in the re-combined beam path into electronic signals, logic circuitry for providing electronic data equivalents to the natural logarithm of the ratio of the energies of the beams in the re-combined beam path directed onto the detector, multi-channel electronic operating and read-out circuitry each channel of which is individually selectable for connection to the logic circuitry and corresponds to measurements at one of the narrow ranges of wavelength selected by the narrow range wavlength selection means, means connecting the channel selection means for the multi-channel electronic operating and read-out circuitry with the narrow range wavelength selection means to effect the required correspondence at each selected narrow range of wavelength and means interconnecting the operating and read-out circuitry of the channels for transfer of stored and/or derived electronic data therebetween.

The invention also consists in apparatus according to the preceding paragraph in which there are provided four channels in the multi-channel operating and read-out circuitry said channels corresponding to selected absorption wavelengths for water and the fat, protein and lactose constituents of milk.

Figure 2:
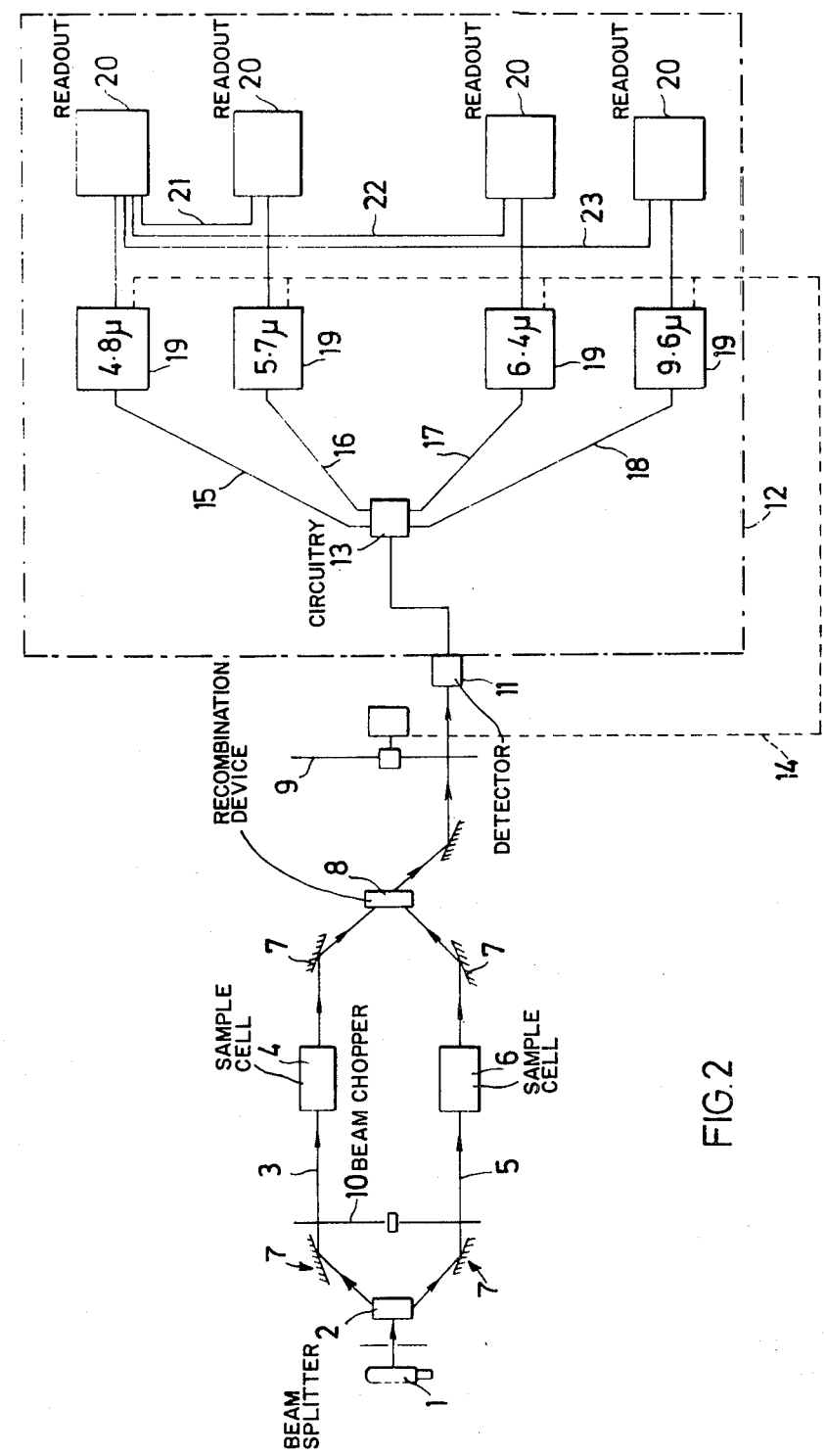

The invention also consists in methods of analysis and apparatus for performing the same substantially as described herein and with reference to the accompanying drawings, of which:

FIG. 1 is a sequence diagram of operations for performing a method of analysis in accordance with one form of the invention; and FIG. 2 is a simple block diagram of apparatus in accordance with the invention for performing the method outlined in FIG. 1.

The invention will now be described with reference to the aforementioned drawings but, in order that the method of analysis to be described may be more fully understood, a simplified mathematical exposition of the steps performed in the method will first be given.

Consider a double beam, infra-red, absorption spectrometer instrument having two beam paths with sample cells of fixed optical path lengths, one in each beam, applied to the analysis of a homogenised milk sample having water as the dispersion medium and fat, protein and lactose as the components of the disperse phase. Let each sample cell be provided with a water sample, and a narrow wavelength range containing the peak absorption wavelength for water of $4.8\mu$ be chosen, then the transmitted intensities of radiation in the beams may be expressed as follows:

Reference beam: $I_1 = \beta_1 I_0 e^{-k_1 c l_1}$

Sample beam: $I_2 = \beta_2 I_0 e^{-k_1 c l_2}$ where $\beta_1$ = attenuation coefficient in reference beam optics.

$\beta_2$ = attenuation coefficient in sample beam optics.

$I_0$ = incident beam intensity for both beams prior to absorption.

$I_1$ = energy of beam transmitted through reference cell.

$I_2$ = energy of beam transmitted through sample cell.

$k_1$ = water absorption coefficient at $4.8\mu$ (water wavelength).

c = concentration of water in the constant path length.

$l_1$ = optical path length through reference cell.

$l_2$ = optical path length through sample cell.

The difference between intensities $I_1$, and $I_2$ is due to optical imbalance, that is $l_1$ not equal to $l_2$ and/or $\beta_1$ not equal to $\beta_2$ and can be corrected by, for example, a trimmer in one beam path to balance the resultant energy. (Alternatively, balance may be effected in the measurement of the beam energies by, for example, electrical circuit back-off means). Thus, at balance, $I_1 = AI_2$ where A = attenuation coefficient due to trimmer $$\therefore \ln \frac{I_1}{I_2} A = k_1 c (l_2 - l_1) + \ln\beta_1 - \ln\beta_2 - \ln A \quad (1)$$

= 0 at balance. (Natural logarithm of ratio 1)

(Note that for most wavelengths other than the narrow wavelength range containing $4.8\mu$, for example, narrow ranges of wavelength containing the wavelengths $5.7\mu$, $6.4\beta$ and $9.6\mu$, which are respectively the peak absorption wavelengths for fat, protein and lactose in milk, $$\ln \frac{I_1}{I_2} A = k_x c (l_2 - l_1) + \ln\beta_1 - \ln\beta_2 - \ln A$$

$$\begin{bmatrix} \text{where } k_x \text{ is the water absorption} \\ \text{coefficient at wavelengths other} \\ \text{than } 4.8\mu \\ \neq 0 \end{bmatrix}$$

since $k_x$ differs at these wavelengths from its value $k_1$ at $4.8\mu$).

Next consider an homogenised milk sample to be inserted into the sample cell in the sample beam whilst the narrow range of wavelength containing $4.8\mu$ is still selected. Then, Reference beam: $I_1 = \beta_1 I_0 e^{-k_1 c l_1}$ \quad (2)

Sample Beam: $AI_3 = \alpha\beta_2 AI_0 e^{-k_1(c-a)l_2}$ \quad (3)

where

A = attenuation coefficient due to trimmer.

$\alpha$ = attenuation coefficient due to scatter.

and a = the fraction by which the mass of water has been changed in the constant path length, that is the fractional change in water concentration. Taking the natural logarithm of the ratio $$\frac{(2)}{(3)}$$

$$\therefore \ln \frac{I_1}{I_3} A = -k_1 c l_1 + k_1 c l_2 - k_1 a l_2 - \ln\alpha\beta_2 A + \ln\beta_1 \quad (4)$$

$$= k_1 c (l_2 - l_1) - k_1 a l_2 - \ln\alpha - \ln\beta_2 - \ln A + \ln\beta_1$$

From (1) above, $$k_1c(l_2-l_1)+l_n\beta_1-l_n\beta_2-l_nA=0$$

and for insignificant scatter (due to homogenisation), $$l_n\alpha=0$$

substituting in (4).

$$l_n\frac{I_1}{I_3}A = -k_1 al_2 \quad (5)$$

If the wavelength selection is now altered to select respectively the narrow ranges of wavelength containing 5.7μ, 6.4μ and 9.6μ (the selected disperse phase component wavelengths), then, Reference beam: $I_4=\beta_1 I_0 e^{-k_x c l_1}$ (6)

Sample beam: $AI_5=\alpha'A\beta_2 I_0 e^{-k_x(c-a)l_2-k\,comp\,bl_2}$ (7)

where $k_x$ = water absorption coefficient at component wavelength.
$k$ comp = component absorption coefficient
$b$ = component concentration
$\alpha'$ = attenuation coefficient due to scatter at the component wavelength, and taking the natural logarithms of the ratio, $$l_n\frac{I_4}{I_5}A = \underbrace{k_x c (l_2 - l_1) - l_n A - l_n\beta_2 + l_n\beta_1}_{\text{optical zero error}} \quad (8)$$

$$\underbrace{-k_x al_2}_{\text{displacement term}} \quad \underbrace{+k\,comp\,bl_2}_{\text{component absorbance}}$$

$$\underbrace{-l_n\alpha'}_{\text{scatter term}}$$

The individual terms in expression (8) may now be considered:

Optical zero error: $k_x c(l_2-l_1)-l_n A-l_n\beta_2+l_n\beta_1$

This term may be eliminated for any wavelength at which $k_x$ applies by adjustment of backing-off means at the wavelength in question whilst a water sample is in each sample cell.

Displacement term: $k_x al_2$
Now $k_x$ = constant × $k_1$
∴ $-k_x al_2$ = -const. × $k_1 al_2$ This term can therefore be eliminated by storing the absorbance at the water wavelength, $k_1 al_2$, multiplying it by a constant equal to $$\frac{k_x}{k_1},$$

and adding it to the logarithmic ratio $$l_n\frac{I_4}{I_5}$$

expression derived at (8) above. The multiplying constant, it is evident, is different for each disperse phase component since it includes $k_x$.

Scatter term: $-l_n\alpha'$

For many samples this term may be rendered insignificant by homogenisation of the sample.

The expression (8) for the logarithmic ratio thus $$l_n\frac{I_4}{I_5}A = -k_x al_2 + \text{const} \times k_1 al_2 + k\,comp\,bl_2 \quad (9)$$

$$\therefore l_n\frac{I_4}{I_5}A = k\,comp\,bl_2$$

Referring now to FIG. 1 of the drawings, the first step (A) in the preferred method of analysing an homogenised milk sample according to the invention comprises providing a sample of water in each path of a double beam spectrometer the output of which is fed to multiple channel electronic measuring circuitry having the further capability of performing mathematical operations.

Apparatus according to the invention for carrying out the preferred method is shown diagrammatically in FIG. 2, where infra-red radiation from a source 1 is divided by a beam splitting device 2 and mirrors 7 into a beam path 3 passing through a sample cell 4 and a beam path 5 passing through a sample cell 6. After passing through the samples the beam paths are re-combined by way of mirrors 7 in a recombination device 8, and thence pass through a narrow wavelength range selection device 9. The latter preferably comprises an interference filter selection disc.

A beam chopping device 10 is included to enable energy to fall intermittently upon a detector 11 alternately from each beam path. The "dark" intervals when neither beam falls upon the detector enable a reference level to be set in the measurement operations. The optical data received by detector 11 is converted to electronic signals which are subsequently handled by multichannel electronic circuitry outlined by the chain-dotted box 12.

Circuitry 13, receiving the electrical output from detector 11, operates to provide at its output a signal representing the natural logarithms of the ratio of the energies of the transmitted beams falling on detector 11. The output of circuitry 13 is directed to four channels, 15, 16, 17 and 18 corresponding to the wavelength ranges required for the analysis operation, as indicated by references 19. Switches in the channels 15-18 linked to device 9 as indicated by dashed line 14 direct the output signal from circuitry 13 only to the channel appropriate to the filter selected by device 9. The channels further contain operating and read-out circuits 20.

The preferred narrow range of wavelength initially chosen for step A is 4.8μ, referred to subsequently for convenience as the absorption at the water wavelength, and this selection is made by turning the disc of device 9 until the appropriate filter lies in the recombined beam path. The apparatus is balanced to give a zero read-out for the water wavelength 4.8μ by means of backing-off and scaling arrangements in the circuit 20 of channel 15. Similar balances are then effected successively for the absorption wavelengths for fat (5.7μ), protein (6.4μ) and lactose (9.6μ) by selection of the appropriate filter in device 9 and adjustment of the backing-off arrangements in the corresponding channel 16, 17 and 18 respectively. The optical zero error for the apparatus at all wavelengths of interest is thus eliminated in step A.

In step B, the water in sample cell 6 is replaced by an homogenised milk sample to be analysed. The two beams are passed through cells 4 and 6 and the narrow wavelength range containing 4.8μ is again chosen. The resultant imbalance read out at circuit 20 in channel 15 is proportional to the absorbance at the water wavelength and this value is stored.

In step C, the wavelength range selector is switched to include the absorption wavelength for fat, 5.7μ, whilst water is retained in cell 4 and the milk sample is retained in cell 6. The resultant imbalance in the logarithmic ratio of the beam intensities derived in channel 16 corresponds to the absorbance due to fat in the milk sample. An addition is made to this absorbance in circuit 20, however, the factor added being the product of the stored absorbance in channel 15 (obtained by way of line 21) and the ratio of the water absorption coefficient at the component wavelength to the water absorption coefficient at the water wavelength. This latter ratio, $$\frac{k_x}{k_1},$$

is a constant ratio for the channel 16 and is pre-set for the operation performed in circuit 20. The result of this operation is that the percentage concentration of fat which is proportional to the absorbance may be obtained at the read-out for channel 16.

Steps D and E are similar to step C except that the narrow ranges of wavelength corresponding to the protein and lactose absorption wavelengths respectively are selected. The pre-set ratios of the water absorption coefficients in channels 17 and 18 differ from the ratio set for channel 16 but the same stored absorbance value from channel 15 is used in each case, being transferred via lines 22, 23 respectively. Thus the percentage concentration of protein and lactose, which is proportional to their relative absorbances, may be read out from circuits 20 in channels 17 and 18.

In the preferred method of analysis a final step F consists of re-selecting the narrow range of wavelength containing the absorption at the water wavelength, 4.8μ, whilst maintaining water in cell 4 and the milk sample in cell 6. A reading for the logarithm of the ratio of the beam intensities is then obtained which represents the total solids content of the milk sample. Alternatively, the total solids content may be derived by addition of the component values obtained in steps C, D and E, neglecting any mineral content in the sample.

Whilst the specific embodiment of the invention has been described as applied to the analysis of milk, the invention is not limited to analysis of this particular substance but is generally applicable to emulsions, suspensions or mixtures of such fluids having a solids content.

We claim:

1. Apparatus for the quantitative estimation of the dispersion medium and one or more components forming the disperse phase of an emulsion or suspension or mixture thereof comprising a double beam, infra-red absorption spectrometer instrument having an infra-red source, beam splitting means providing two beam paths of infra-red radiation from the source, a first sample cell disposed in a first of the beam paths and a second sample cell disposed in the second of the beam paths, re-combination means for the beams subsequent to their passage through the cells to provide a single re-combined beam path, a beam chopping device interacting with the two beam paths prior to recombination, narrow range wavelength selection means positioned to limit the wavelength range of radiation in the re-combined beam path, a detector for converting the optical data in the re-combined beam path into electronic signals, conversion circuitry for providing electronic data equivalents to the natural logarithm of the ratio of the energies of the beams in the re-combined beam path directed onto the detector, multi-channel electronic operating and read-out circuitry each channel of which is individually selectable for connection to the conversion circuitry and corresponds to measurements at one of the narrow ranges of wavelength selected by the narrow range wavelength selection means, means connecting the channel selection means for the multi-channel electronic operating and read-out circuitry with the narrow range wavelength selection means to effect the required correspondence at each selected narrow range of wavelength, means interconnecting the operating and read-out circuitry of the channels for transfer of stored and/or derived electronic data therebetween and means for storing, in each channel of the multi-channel electronic operating means associated with the narrow range of wavelength containing the peak absorption wavelength of a disperse phase component under assessment by that channel, the appropriate predetermined ratio of the absorption coefficient of the dispersion medium at the narrow range of wavelength selected for the channel concerned to the absorption coefficient of the dispersion medium at a chosen narrow range of wavelength associated with a channel for the assessment of dispersion medium absorbance.

2. Apparatus as claimed in claim 1 in which there are provided four channels in the multi-channel operating and read-out circuitry, said channels corresponding to selected absorption wavelengths for water and the fat, protein and lactose constituents of milk.

* * * * *